US00PP27572P3

(12) United States Plant Patent
Danziger

(10) Patent No.: US PP27,572 P3
(45) Date of Patent: Jan. 17, 2017

(54) ***SUTERA* PLANT NAMED 'DCOPDBINDG'**

(50) Latin Name: *Sutera cordata*
Varietal Denomination: DCOPDBINDG

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 74 days.

(21) Appl. No.: 14/545,102

(22) Filed: Mar. 27, 2015

(65) Prior Publication Data

US 2016/0286709 P1 Sep. 29, 2016

(51) Int. Cl.
*A01H 5/02* (2006.01)

(52) U.S. Cl.
USPC ..... Plt./485

(58) Field of Classification Search
USPC ..... Plt./485
See application file for complete search history.

*Primary Examiner* — Susan McCormick Ewoldt
(74) *Attorney, Agent, or Firm* — Cassandra Bright

(57) ABSTRACT

A new and distinct *Sutera* cultivar named 'DCOPDBINDG' is disclosed, characterized by early and abundant large violet-blue double flowers, medium plant vigor and a mounded and well branched growth habit. The new variety is a *Sutera*, normally produced as an outdoor garden or container plant.

2 Drawing Sheets

Figure 1:
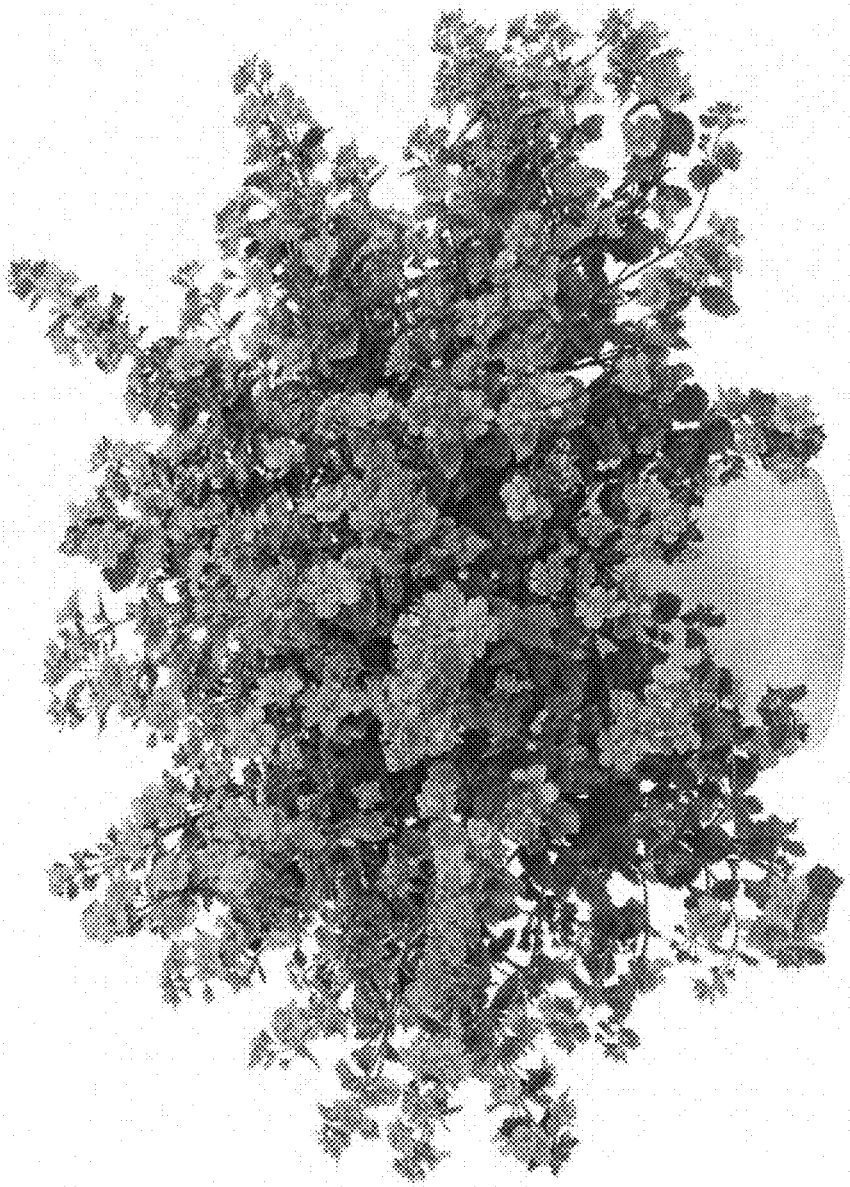

Latin name of the genus and species: *Sutera cordata*.
Variety denomination: 'DCOPDBINDG'.

BACKGROUND OF THE INVENTION

The new *Sutera* cultivar is a product of a planned breeding program conducted by the inventor, Gavriel Danziger, in Moshav Mishmar Hashiva, Israel. The objective of the breeding program was to produce new *Sutera* varieties for ornamental commercial applications. The open pollination resulting in this new variety was made during May of 2010.

The seed parent is the, unpatented, proprietary variety referred to as *Sutera* 'cv. 10-1725'. The pollen parent is unknown as it was an open pollination breeding program. The new variety was discovered in March of 2011 by the inventor in a group of seedlings resulting from the 2010 open pollination, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in March of 2011 and has shown that the unique features of this cultivar are stable and reproduced true to type in more than 20 successive generations.

SUMMARY OF THE INVENTION

The cultivar 'DCOPDBINDG' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCOPDBINDG' These characteristics in combination distinguish 'DCOPDBINDG' as a new and distinct *Sutera* cultivar:

1. Mounded growth habit.
2. Large Violet-Blue double flowers.

3. Well branched plants
4. Early abundant flowering.
5. Medium vigor.

Plants of the new cultivar 'DCOPDBINDG' are similar to plants of the seed parent, *Sutera* 'cv. 10-1725' in most horticultural characteristics, however, plants of the new cultivar 'DCOPDBINDG' differ in the following;

1. Plant habit is mounded. The parent habit is semi-trailing.
2. Large, Violet-Blue double flowers. The parent has medium sized, lavender, semi-double flowers.
3. More abundant flowering than the parent.

COMMERCIAL COMPARISON

Plants of the new cultivar 'DCOPDBINDG' are comparable to the commercial variety *Sutera* 'DANDCOP41' U.S. Plant Pat. No. 23,146. The two *Sutera* varieties are similar in most horticultural characteristics; however, the new variety 'DCOPDBINDG' differs in the following:

1. The new variety 'DCOPDBINDG' has a less compact plant habit than this comparator.
2. Comparison variety has large, white flowers whereas the new variety 'DCOPDBINDG' has large, violet-blue flowers.
3. Comparison variety produces more branches per plant.
4. Comparison variety plant is shorter than the new variety.
5. Comparison variety has strong vigor whereas the new variety has medium vigor.

Plants of the new cultivar 'DCOPDBINDG' can also be comparable to the unpatented commercial variety *Sutera* 'DANCOP48'. The two *Sutera* varieties are similar in most horticultural characteristics; however, the new variety 'DCOPDBINDG' differs in the following:

1. Comparison variety has a semi-trailing, elongated growth habit whereas the candidate variety has a mounded growth habit.

2. Comparison variety has extra-large, white flowers whereas the new variety 'DCOPDBINDG' has large, violet-blue flowers.
3. The new variety 'DCOPDBINDG' variety produces less branches per plant than the comparison variety.
4. Comparison variety flowers later than the new variety 'DCOPDBINDG'.
5. Comparison variety has strong vigor whereas the new variety 'DCOPDBINDG' has medium vigor.

BRIEF DESCRIPTION OF THE PHOTOGRAPHS

The accompanying photograph in FIG. 1 illustrates in full color a typical plant of 'DCOPDBINDG' grown in a greenhouse, in a 13 cm pot. Age of the plant photographed is approximately 3 months old from a rooted cutting.

Figure 2:
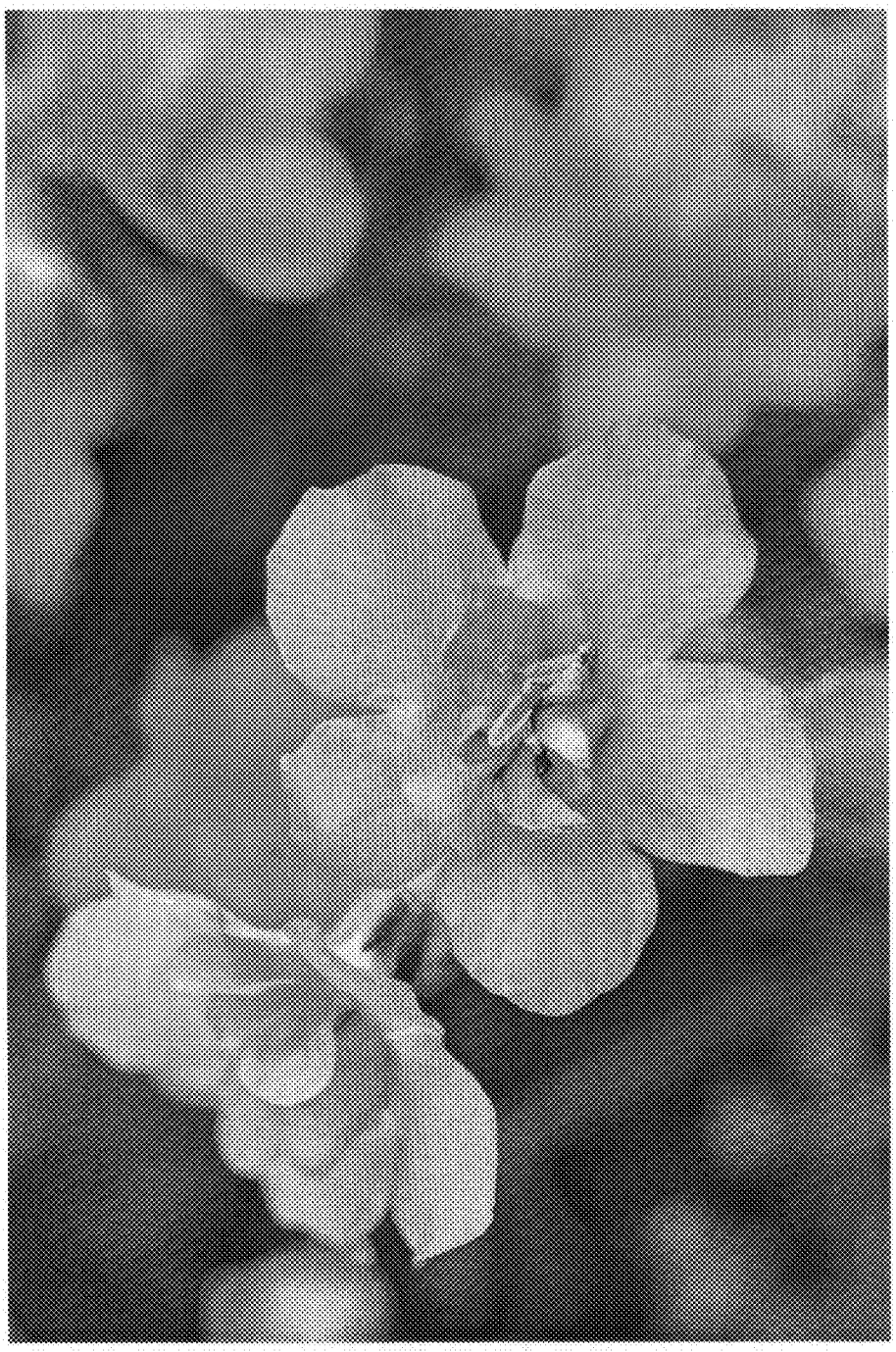

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DCOPDBINDG' plants grown in the Winter to Spring in moderate climate in a greenhouse, in Moshav Mishmar Hashiva, Israel. The growing temperature ranged from 15° C. to 26° C. during the day and from 13° C. to 16° C. during the night. General light conditions are normal sunlight and numerical values represent averages of typical plant types.

Botanical classification: *Sutera cordata* 'DCOPDBINDG'.

PROPAGATION

Type of propagation typically used: Cutting.
Time to initiate roots: 7-10 days at approximately 20° C.
Root description: Fine, fibrous roots.

PLANT

Age of plant described: Approximately 3 months from rooted cutting.
Container size of the plant described: 13 cm.
Growth habit: Semi-trailing and vigorous.
Height: Approximately 24 cm.
Plant spread: Approximately 55 cm.
Growth rate: Moderate.
Characteristics of primary lateral branches:
- *Quantity*.—About 8.
- *Form*.—Cylindrical.
- *Diameter*.—About 0.2 cm.
- *Color*.—RHS Yellow-Green 144 A.
- *Texture*.—Velvety.
- *Strength*.—Flexible, not easily broken.

Internode length: About 2 cm.

FOLIAGE

Leaf:
- *Arrangement*.—Opposite, petiolate.
- *Quantity*.—Approximately 50 per branch.
- *Average length*.—2.5 cm.
- *Average width*.—1.8 cm.
- *Shape of blade*.—Ovate.
- *Apex*.—Obtuse.
- *Base*.—Acuminate.
- *Margin*.—Serrate.
- *Texture of top surface*.—Velvety.
- *Texture of bottom surface*.—Velvety.
- *Pubescence*.—Slightly pubescent.
- *Aspect*.—About 90° to the branch.
- *Color*.—Young foliage upper side: RHS Green 137 B. Young foliage under side: RHS Green 137 C. Mature foliage upper side: RHS Green 137 A. Mature foliage under side: RHS Green 137 B.
- *Venation*.—Type: Pinnate. Venation color upper side: RHS Green 137 A. Venation color under side: RHS Green 137 C.
- *Petiole*.—Length: About 0.5 cm. Diameter: About 0.2 cm. Color: RHS Green 137 A.
- *Texture*.—Slightly velvety.

FLOWER

Natural flowering season: All year round under mild Mediterranean conditions.
Days to flowering from rooted cutting: About 45.
Inflorescence and flower type and habit: Axillary, solitary, salverform double flowers.
Rate of flower opening: 3 to 5 days from bud to fully opened flower.
Flower longevity on plant: About 7 days.
Persistent or self-cleaning: Persistent.
Bud:
- *Shape*.—Spatulate.
- *Length*.—About 0.7 cm.
- *Diameter*.—About 0.4 cm.
- *Color*.—RHS Violet-Blue 92 A.

Flower size:
- *Diameter*.—About 2.0 cm.
- *Length*.—About 1.3 cm.
- *Corolla tube diameter*.—About 0.3 cm.

Corolla/petals:
- *Arrangement*.—Symmetric.
- *Lobe length*.—About 0.8 cm.
- *Lobe width*.—About 0.7 cm.
- *Quantity*.—5 large, fully expanded, with an additional 5 curled in the center of the flower.
- *Texture*.—Velvety.
- *Lobe apex*.—Rounded.
- *Lobe shape*.—Rounded.
- *Margin*.—Entire.
- *Aspect*.—About 90° to the tube.

Color:
- *When opening*.—Upper surface: RHS Violet N 87 B. Lower surface: RHS Violet N 87 C.
- *Fully opened*.—Upper surface: RHS Violet N 87 B. Lower surface: RHS Violet N 87 C.
- *Visible (outside) corolla tube color*.—RHS Yellow 13 A. Inside is not visible due to the extra petals of the double flower).

Calyx/sepals:
- *Quantity per flower*.—5.
- *Shape*.—Linear.
- *Length*.—About 0.4 cm.
- *Width*.—About 0.1 cm.

*Apex*.—Acute.
*Base*.—Fused.
*Margin*.—Entire.
*Texture*.—Slightly velvety.
*Color*.—Upper Surface: RHS Green 137 B. Lower Surface: RHS Green 137 C.

Peduncle: None.

Pedicel:
*Length*.—Approximately 1.0 cm.
*Diameter*.—Approximately 0.1 cm.
*Color*.—Near RHS Green 137 C.
*Orientation*.—Slanted upward and outward.
*Pubescence*.—Slightly pubescent.

Fragrance: None.

REPRODUCTIVE ORGANS

Stamens:
*Number*.—4.
*Filament length*.—Approximately 0.6 cm.

Anthers:
*Shape*.—Cylindrical.
*Length*.—Approximately 0.1 cm.
*Width*.—Less than 0.1 cm.
*Color*.—RHS Yellow 7 A.
*Pollen*.—Color: RHS Yellow 7 C. Quantity: Sparse.

Pistil:
*Number*.—1.
*Length*.—About 1.1 cm.
*Style*.—Length: About 1 cm. Color: RHS Green-Yellow 1 C.
*Stigma*.—Shape: Undulate. Color: RHS Green-Yellow 1 A. Ovary Color: RHS Yellow-Green 143 C.

OTHER CHARACTERISTICS

Seeds and fruits: About 20 elliptic, small (1 mm long) Brown seeds per one elliptic Brown capsule. Colors not accurately measured with R.H.S. chart.

Disease/pest resistance: Neither resistance nor susceptibility to pathogens and pests common to *Sutera* have been observed.

Temperature tolerance: The new variety tolerates temperatures between 5 to 40° C.

What is claimed is:

1. A new and distinct cultivar of *Sutera* plant named 'DCOPDBINDG' as herein illustrated and described.

* * * * *